(12) United States Patent
Miller et al.

(10) Patent No.: US 7,968,755 B2
(45) Date of Patent: Jun. 28, 2011

(54) PROCESS AND CATALYST FOR CONVERTING ALKANES

(75) Inventors: Jorge Miller, Houston, TX (US); Luisa Kling Miller, Houston, TX (US)

(73) Assignee: Sajet Development LLC, Houston, TX (US)

( * ) Notice: Subject to any disclaimer, the term of this patent is extended or adjusted under 35 U.S.C. 154(b) by 0 days.

(21) Appl. No.: 12/874,185

(22) Filed: Sep. 1, 2010

(65) Prior Publication Data

US 2010/0331582 A1    Dec. 30, 2010

Related U.S. Application Data

(63) Continuation of application No. 12/571,681, filed on Oct. 1, 2009, now Pat. No. 7,812,201.

(60) Provisional application No. 61/194,866, filed on Oct. 1, 2008, provisional application No. 61/211,579, filed on Apr. 1, 2009, provisional application No. 61/273,308, filed on Aug. 3, 2009.

(51) Int. Cl.
*C07C 27/00* (2006.01)
(52) U.S. Cl. .................. 568/891; 568/851; 568/910
(58) Field of Classification Search .................. None
See application file for complete search history.

(56) References Cited

U.S. PATENT DOCUMENTS

| | | | |
|---|---|---|---|
| 3,172,915 A | 3/1965 | Borkowski et al. |
| 3,689,577 A | 9/1972 | Selwitz |
| 4,039,597 A | 8/1977 | Tsao |
| 4,452,678 A | 6/1984 | Ollivier |
| 4,456,778 A | 6/1984 | Zolffel et al. |
| 4,523,040 A | 6/1985 | Olah |
| 4,814,527 A | 3/1989 | Diesen |
| 4,895,680 A | 1/1990 | Ellis, Jr. et al. |
| 4,895,682 A | 1/1990 | Ellis, Jr. et al. |
| 4,900,871 A | 2/1990 | Ellis, Jr. et al. |
| 4,918,249 A | 4/1990 | Durante et al. |
| 4,971,664 A | 11/1990 | Turro et al. |
| 4,982,023 A | 1/1991 | Han et al. |
| 4,990,696 A | 2/1991 | Stauffer |
| 5,012,029 A | 4/1991 | Han et al. |
| 5,068,478 A | 11/1991 | Miller et al. |
| 5,068,485 A | 11/1991 | Iton et al. |
| 5,099,084 A | 3/1992 | Stauffer |
| 5,109,138 A | 4/1992 | Holbrook et al. |
| 5,131,985 A | 7/1992 | Berg et al. |
| 5,132,474 A | 7/1992 | Mashio |
| 5,152,876 A | 10/1992 | Berg et al. |
| 5,185,479 A | 2/1993 | Stauffer |
| 5,196,094 A | 3/1993 | Berg et al. |
| 5,198,121 A | 3/1993 | Masini et al. |
| 5,220,080 A | 6/1993 | Lyons et al. |
| 5,243,098 A | 9/1993 | Miller et al. |
| 5,276,226 A | 1/1994 | Horvath et al. |
| 5,302,773 A | 4/1994 | Vrieland et al. |
| 5,321,187 A | 6/1994 | Orvalles et al. |
| 5,334,777 A | 8/1994 | Miller et al. |
| 5,345,010 A | 9/1994 | Lyons et al. |
| 5,354,916 A | 10/1994 | Horvath et al. |
| 5,436,378 A | 7/1995 | Masini et al. |
| 5,723,697 A | 3/1998 | Bhinde et al. |
| 5,998,679 A | 12/1999 | Miller |
| 6,008,421 A | 12/1999 | Larsen et al. |
| 6,137,017 A | 10/2000 | Stauffer |
| 6,380,444 B1 | 4/2002 | Bjerrum et al. |
| 6,403,840 B1 | 6/2002 | Zhou et al. |
| 6,452,058 B1 | 9/2002 | Schweizer et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,572 B1 | 10/2002 | Zhou et al. |
| 6,482,989 B2 | 11/2002 | Murahasi et al. |
| 6,486,368 B1 | 11/2002 | Zhou et al. |
| 6,525,230 B2 | 2/2003 | Grosso |
| 6,713,655 B2 | 3/2004 | Yilmaz et al. |
| 7,019,182 B2 | 3/2006 | Grosso |
| 7,064,238 B2 | 6/2006 | Waycuilis |
| 7,091,387 B2 | 8/2006 | Fong et al. |
| 7,148,390 B2 | 12/2006 | Zhou et al. |
| 7,161,050 B2 | 1/2007 | Sherman et al. |
| 7,230,150 B2 | 6/2007 | Grosso et al. |
| 7,348,464 B2 | 3/2008 | Waycuilis |
| 7,361,794 B2 | 4/2008 | Grosso |
| 7,456,327 B2 | 11/2008 | Pawlak et al. |
| 7,812,201 B2 * | 10/2010 | Miller et al. .................. 568/891 |
| 2002/0156328 A1 | 10/2002 | Grosso |
| 2002/0198416 A1 | 12/2002 | Zhou et al. |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125585 A1 | 7/2003 | Yilmaz et al. |
| 2003/0125589 A1 | 7/2003 | Grosso |
| 2003/0166973 A1 | 9/2003 | Zhou et al. |
| 2004/0006246 A1 | 1/2004 | Sherman et al. |
| 2005/0187410 A1 | 8/2005 | Shan et al. |

(Continued)

FOREIGN PATENT DOCUMENTS

WO    WO 83/00859    3/1983

(Continued)

*Primary Examiner* — Brian J Davis
(74) *Attorney, Agent, or Firm* — Baker & McKenzie LLP

(57) ABSTRACT

Methods and catalysts for producing alcohols, ethers, and/or alkenes from alkanes are provided. More particularly, novel caged, or encapsulated, metal oxide catalysts and processes utilizing such catalysts to convert alkanes to alcohols and/or ethers and to convert alcohols and/or ethers to alkenes are provided.

11 Claims, 1 Drawing Sheet

U.S. PATENT DOCUMENTS

| | | |
|---|---|---|
| 2005/0192468 A1 | 9/2005 | Sherman et al. |
| 2005/0215837 A1 | 9/2005 | Hoffpauir et al. |
| 2005/0245771 A1 | 11/2005 | Fong et al. |
| 2005/0245772 A1 | 11/2005 | Fong et al. |
| 2006/0009662 A1 | 1/2006 | Waycuilis |
| 2006/0069169 A1 | 3/2006 | Li et al. |
| 2006/0100469 A1 | 5/2006 | Waycuilis |
| 2006/0229475 A1 | 10/2006 | Weiss et al. |
| 2007/0149833 A1 | 6/2007 | Brandvold et al. |
| 2007/0167533 A1 | 7/2007 | Pawlak et al. |
| 2007/0238909 A1 | 10/2007 | Gadewar et al. |
| 2008/0188701 A1 | 8/2008 | Qi et al. |
| 2008/0200740 A1 | 8/2008 | Waycuilis |
| 2008/0275279 A1 | 11/2008 | Podkolzin et al. |
| 2008/0275284 A1 | 11/2008 | Waycuilis |
| 2008/0314758 A1 | 12/2008 | Grosso et al. |
| 2009/0005620 A1 | 1/2009 | Waycuilis et al. |
| 2009/0137857 A1 | 5/2009 | Xie et al. |

FOREIGN PATENT DOCUMENTS

| | | |
|---|---|---|
| WO | WO 91/17971 | 11/1991 |
| WO | WO 91/18856 | 12/1991 |
| WO | WO 92/03225 | 3/1992 |
| WO | WO 93/21141 | 10/1993 |
| WO | WO 94/09897 | 5/1994 |
| WO | WO 96/07626 | 3/1996 |
| WO | WO 96/15086 | 5/1996 |
| WO | WO 97/11928 | 4/1997 |
| WO | WO 99/24383 | 5/1999 |
| WO | WO 99/59946 | 11/1999 |
| WO | WO 02/20434 | 3/2002 |
| WO | WO 02/094751 | 11/2002 |
| WO | WO 03/000635 | 1/2003 |
| WO | WO 03/062172 | 7/2003 |
| WO | WO 2005/095310 | 10/2005 |
| WO | WO 2005/110953 | 11/2005 |
| WO | WO 2006/069108 | 6/2006 |
| WO | WO 2006/110697 | 10/2006 |
| WO | WO 2006/118935 | 11/2006 |
| WO | WO 2007/046986 | 4/2007 |
| WO | WO 2007/094995 | 8/2007 |
| WO | WO 2008/143940 | 11/2008 |

* cited by examiner

PROCESS AND CATALYST FOR CONVERTING ALKANES

RELATED APPLICATIONS

This application is a continuation of U.S. application Ser. No. 12/571681, filed on Oct. 1, 2009 now U.S. Pat. No. 7,812,201, and claims priority to U.S. Provisional Application Nos. 61/194,866 filed on Oct. 1, 2008; 61/211,579, filed on Apr. 1, 2009; and 61/273,308, filed on Aug. 3, 2009, the disclosures of which are incorporated herein by reference.

BACKGROUND OF THE INVENTION

The invention relates to methods and catalysts for producing alcohols, ethers, and/or alkenes from alkanes. More particularly, the invention relates to a novel caged, or encapsulated, metal oxide catalysts and processes utilizing such catalysts. This invention further relates to a process to convert alkanes to alcohols and/or ethers to alkenes.

Lower alkenes, such as ethylene, propylene and butylene are used for a variety of applications. For example, ethylene is one of the most produced organic compound in the world, with the majority of ethylene being used to produce ethylene oxide, ethylene dichloride, and polyethylene. Lower alkenes may be recovered from petroleum by fractional distillation but demand far exceeds recovery by this method. Therefore, the majority of lower alkenes are produced by energy intensive cracking processes that are well known in the art. For example, ethylene is commonly produced in the petrochemical industry by steam cracking in which gaseous or light liquid hydrocarbons are heated to 700-950° C., in the presence of steam followed by rapid cooling, thereby converting large hydrocarbons into smaller ones and introducing unsaturation. Ethylene is then separated from the resulting product mixture by repeated compression and distillation. More recently, efforts to overcome the energy requirements and other issues, such as $CO_2$ issues, related to steam cracking, have resulted in processes involving catalytic cracking using a fluid-bed catalyst such as those processes described in U.S. Patent Publication No. 20090137857.

Other methods are known for producing alkenes, such as from acid dehydration of alcohols, are also well known. Such methods, however, have heretofore, only been practical in laboratory, and not industrial, settings and quantities. In such laboratory methods, alcohols may be formed by reaction of alkyl halides and metal hydroxides. For example, U.S. Pat. No. 5,334,777 shows the reaction of methyl chloride in the vapor phase with magnesium oxide and with magnesium oxide zeolite. U.S. Pat. No. 3,172,915 discloses the use of ferric oxide as a base to react with methyl chloride to form methyl alcohol, while U.S. Pat. No. 5,998,679 discloses a process in which ferric hydroxide is used as a base to react in the liquid phase with methyl bromide. Finally, U.S. Pat. Nos. 6,462,243; 6,465,696; 6,472,572; 6,486,368; 6,403,840; and 6,525,230 all disclose a process in which alkyl bromides are reacted with a metallic oxide to form alcohols and other products, such as di-methyl ether. All of these processes remain impractical for industrial use due mainly to catalyst attrition and over-halogenation problems resulting in the need for expensive re-crystallation.

There remains a need, therefore, for a process to form alcohol, ether or alkene at commercially practicable rates, with minimization or elimination of formation of other related compounds, and specially higher halides. There is a further need for catalysts to effectuate such process while minimizing or preventing the simultaneous production of higher halides during alcohol or alkene formation.

SUMMARY OF THE INVENTION

In one aspect of the invention provide a process to convert alkanes into alcohols and/or ethers including halogenating one or more alkanes with one or more halogens to form one or more alkane halides and one or more hydrogen halide acids; and reacting the alkane halides and hydrogen halide acid with one or more encapsulated metal oxide catalysts to form one or more compounds selected from the group of alkyl alcohols, ethers and alkenes and one or more metal halide; wherein the one or more encapsulated metal oxide catalysts comprises a pelletized and calcined mixture of an encapsulating material and an organic metal salt. In specific embodiments of the invention, the organic metal salt is selected from magnesium citrate and magnesium stearate. In certain embodiments, the encapsulating material is selected from bentonite, bauxite, and kaolin clays.

In another aspect of the invention, alkanes are further converted to alkenes by further conversion of the alcohols and/or ethers to alkenes by use of an appropriate catalyst. In some embodiments, the encapsulating material functions as a catalyst to convert alcohols and/or ethers to alkenes. In specific embodiments of the invention, the encapsulating material is process of claim 1 wherein the clay is bentonite.

In another aspect of the invention, a novel catalyst for the conversion of alkanes is provided wherein the catalyst is an encapsulated metal oxide. In certain embodiments of the invention, the encapsulating material is a clay having a pore size of 5 and 300 millimicrons, while in other embodiments, the pore size is between 10 and 100 millimicrons.

DESCRIPTION OF THE PREFERRED EMBODIMENTS

Figure 1:
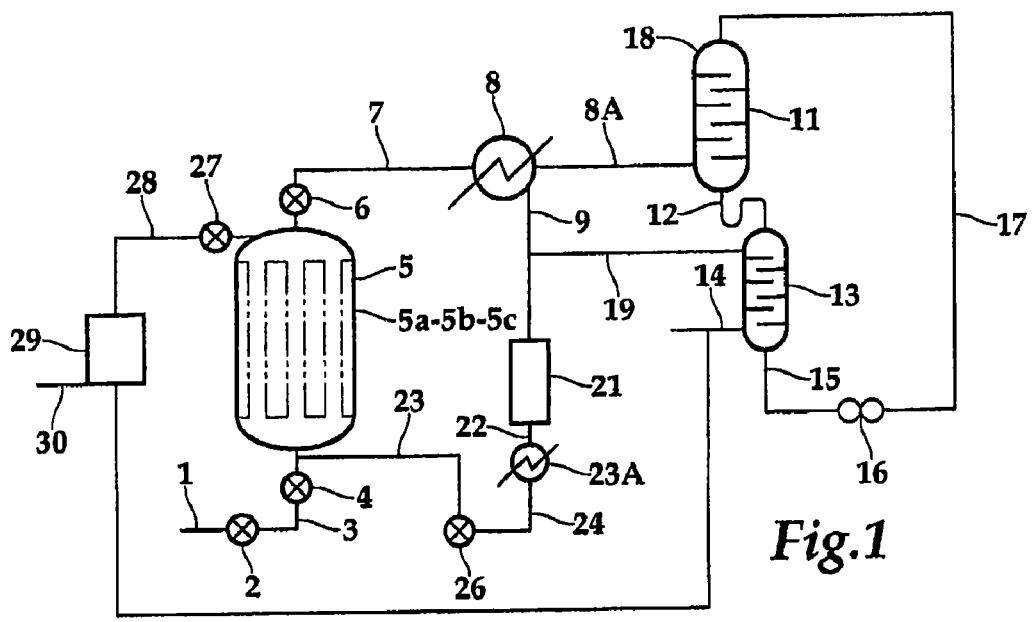
FIG. 1 is a schematic diagram of the one embodiment of the inventive process.

Embodiments of the invention provide novel, highly effective encapsulated metal halide catalyst compositions for the formation of alcohols and alkenes.

In order that the invention be better understood the following equations illustrating the use of chlorine or bromine as the halide, magnesium as the active metal and magnesium chloride hydroxide or magnesium bromide hydroxide as the reacting base are shown:

Chlorination step $$CH_4(g)+Cl_2(g) \rightarrow CH_3Cl(g)+HCl(g)$$

Alcohol formation $$CH_3Cl(g)+HCl(g)+2Mg(OH)Cl+3H_2O(g) \rightarrow CH_3OH(g)+2MgCl_2 \ast 2H_2O$$

Chlorine and base Formation $$2MgCl_2 \ast 2H_2O+O_2(g) \rightarrow 2Mg(OH)Cl+Cl_2(g)+3H_2O(g)$$

Alkene formation $$2CH_3OH(g) \rightarrow C_2H_4(g)+2H_2O(g)$$

The overall reaction is $$2CH_4(g)+O_2(g) \rightarrow C_2H_4(g)+2H_2O$$

Bromination step $$CH_4(g) + Br_2(g) \rightarrow CH_3Br(g) + HBr(g)$$

Alcohol formation $$CH_3Br(g) + HBr(g) + Mg(OH)_2 \rightarrow MgBr_2 \cdot H_2O + CH_3OH(g)$$

Bromine and hydroxide formation $$MgBr_2 \cdot H_2O + 1/2 O_2(g) \rightarrow Mg(OH)_2 + Br_2(g)$$

Alkene formation $$2CH_3OH(g) \rightarrow C_2H_4(g) + 2H_2O(g)$$

As previously discussed processes utilizing these reaction steps have heretofore been commercially impracticable because of attrition. Embodiments of the invention provide encapsulated metal oxide catalysts and processes using such novel catalysts to produce alcohols and alkenes from alkanes. In some embodiments of the invention, the material used to encapsulate the metal oxide catalyst may also function as a catalyst for the conversion of alcohols to alkenes. In certain embodiments of the present invention, one or more metal oxides are encapsulated in clay particles. The encapsulated metal oxide catalyst is produced by mixing one or more insoluble or slightly soluble high molecular volume organic metal salt with one or more porous materials, in a preferred embodiment, a clay material, including without limitation, kaolin, bentonite, and bauxite, and water to form a dough which is then pelletized, dried in air at typical room temperatures. The dried pellets are then heated in air to a temperature between 600° C. and 1000° C. to form a strong ceramic, porous pellet. Because the clay is annealed and hardened, it is important that the pore size be sufficiently large to house the metal halide hydrate, which is formed by exposure of the metal salt to water, without fracturing the clay structure. In preferred embodiments of the invention, the metal salt is a metal organic salt.

Alkanes useful in embodiments of the present invention include any alkanes having one or more carbon atoms. In a preferred embodiment, the alkane is methane. In other embodiments of the invention, the alkane feed includes more than one alkane.

The proportions of the organic metal salt to clay may vary from about 30 wt % clay to metal salt to clay to about 50 wt % metal salt to clay. The higher the proportion of clay to organic metal salt, the harder the pellet but the lower the capacity for alcohol production. The pellets can be made spherical or in any other shape, by hand or by machine techniques known in the art. Other types of clays may be used. The particle size may be any of the known particle sizes for known clays. In a preferred embodiment, the clay particle size is between 1 and 40 millimicrons.

Metals useful in embodiments of the invention may include any alkaline earth, alkali, basic or transition metal. Group 2 metals are preferred and zinc and magnesium are most preferred for use in the metal salt. Any halogen may be used to form the metal salt. Metal chlorides and bromides are used in preferred embodiments of the invention.

In a first preferred embodiment of the invention, the metal halide is magnesium chloride and in a second preferred embodiment the metal halide is magnesium bromide. In yet other embodiments of the invention the metal salt is zinc chloride or zinc bromide. In some embodiments of the invention, one or more metal halides are used wherein the metals may be the same or different metals and the halogen component may be the same or different halogens.

The weight proportion of the clay in the combined mixture of water, clay, and organic metal salt should be at least 30% by weight of clay. The weight percent of water may range from 20% to 30%. The weight percent of the organic metal salt may range from 50% to 70%. Without intending to be bound to any particular theory, it is believed that the clay particles in the mixture provide a highly porous material. For example, if magnesium citrate, having a molar volume of about 460 cubic centimeters per mole, is used as the organic metal salt, the pores left in the pellets formed from the mixture would be sufficient to accommodate the maximum size of the magnesium chloride hydrate, which is 130 cubic centimeters per mole for the hexa-hydrate $MgCl_2 \cdot 6H_2O$. Thus, the clays used to produce the novel catalysts provide sufficiently large openings to accommodate the hexa-hydrate and not burst the clay structure. In a preferred embodiment of the invention, the pore size of the final ceramic clays is between 5 and 300 millimicrons. In a more preferred embodiment, the pore size is between 10 and 100 millimicrons.

Bentonite clay is a known catalyst for alkene formation from alcohols. Thus, when bentonite is used to encapsulate the metal halide hydrate, no additional activation agents are required to catalyze the formation of alkenes from alcohols. Other known clays and/or support structures are also known to catalyze the formation of alkenes from alcohols and the use of such supports and/or clays is within the scope of this invention. For example, montmonillonite, illite, chorite clays and certain phylosilicates also are known to catalyze the conversion of alcohols to alkenes and may be used as the encapsulating material in certain aspects of the invention. In embodiments of the invention utilizing kaolin and/or bauxite, additional activation agents or catalysts must be used to convert the alcohol into alkene.

In those embodiments of the invention in which the encapsulating material does not catalyze the conversion of alcohols to alkenes, or does not catalyze such conversion with adequate efficiency, small amounts, i.e., from 1 wt % to 10% and preferably about 2 wt % of finely ground X-type zeolite (also known as molecular sieves) in the acid form may be added to the mixture prior to formation of the dough and polarization. Alternatively, Y-type zeolite or an excess (i.e., over about 10%) of a finely ground X-type zeolite powder may be added to the mixture prior to formation of the dough and pelletization.

Halogenation of methane may be accomplished by means of any of a number of catalysts known in the art. However, industrially useful catalysts for methane halogenation include ultraviolet light and/or heat. Embodiments of the invention include the use of methyl halides, however produced or supplied. When temperature is used as a catalyst, the temperature for the methane halogenation step may range from 100° C. and 500° C., more preferably from 150° C. to 400° C. and most preferably from 250° C. to 350° C.

For formation of alcohol from the alkane halide utilizing the novel catalysts of the invention, the temperature is preferably between 120° C. and 200° C. but temperatures as low as 100° C. and as high 250° C. may be utilized. Likewise the alcohols may be converted to alkenes in the presence of the encapsulated metal oxide catalysts of the invention at similarly low temperatures, i.e., from between about 100° C. and 300° C., preferably between about 100° C. and 200° C. and most preferably between about 120° C. and 150° C.

FIG. 1 shows schematically one possible process equipment and materials flow for the inventive process. Referring to FIG. 1, to form halide vapor, heated air is led from line 1 and opened valve 2 through line 3 and opened valve 4 to tubular reactor 5. The tubes of tubular reactor 5 contain the inventive encapsulated metal halide. Halide vapor together with excess air leaves reactor 5 through opened valve 6 and is led through line 7 to condenser 8 where most of the alkyl halide is condensed and flows down to line 9. Excess air and nitrogen containing traces of halide are led through line 8a from condenser 8 to absorber 11 where the halide is absorbed and concentrated in an appropriate solvent down flowing through absorber 11. Halide containing solvent flows downwardly through line 12 to stripper 13 where it meets a counter flow of methane coming through line 14 which strips the halide from the down flowing solvent. The halide-stripped solvent leaves stripper 13 through line 15 and is led through pump 16 to line 17 which feeds absorber 11. Excess air and nitrogen are exhausted from absorber 11 trough line 18.

Halide-enriched methane from striper 13 is led through line 19 to line 9 where it meets more halide coming from condenser 8 and together with re-circulated excess methane from line 20 is led into halogenating reactor 21 where they react at the proper temperatures to form methyl halide and hydro-halide acid. Reactor 21 works continuously while reactor 5, 5A, 5B and 5C operate batch wise. Reacted gasses from reactor 21 are led trough line 22 to cooler 23A. Cooled gasses are led through line 24 to a series of reactors 5, (5A, 5B, and 5C not shown) one of which is in the metal basic form. Assuming reactor 5 is in the metal basic form the following procedure follows: Gasses containing methyl halide, hydrohalide acid and excess methane coming from line 24 are led through line 23 and opened valve 26 to reactor 5, valve 6 being closed. Upward moving gasses through reactor 5 react with metal basic form to form ethylene, propylene etc., which together with excess methane are led through opened valve 27 and line 28 to separator 29, where products are separated and delivered through product line 30. Excess methane is led from separator 29 to line 14, again to re-circulate in the system. Separator 29 can include compression, distillation, diffusion process equipment, as known in the art. Other standard equipment, well known in the art such as sampling ports, are not shown.

For continuous operation, besides the halogenation reactor there may preferably be four reactors containing the inventive encapsulated metal halide/metal halide hydroxide catalyst. In a first reactor the metal may be oxidized. These gasses in the second are being displaced with steam and cooled to the temperature of the ethylene reaction. The third reactor is treating the gasses to form alkenes and the forth reactor is being treated with steam to sweep out remaining gasses and also being heated to the oxidation temperature. Steam is also used to displace remaining gasses in the reactors to prevent possible explosions or contaminations.

Figure 2:
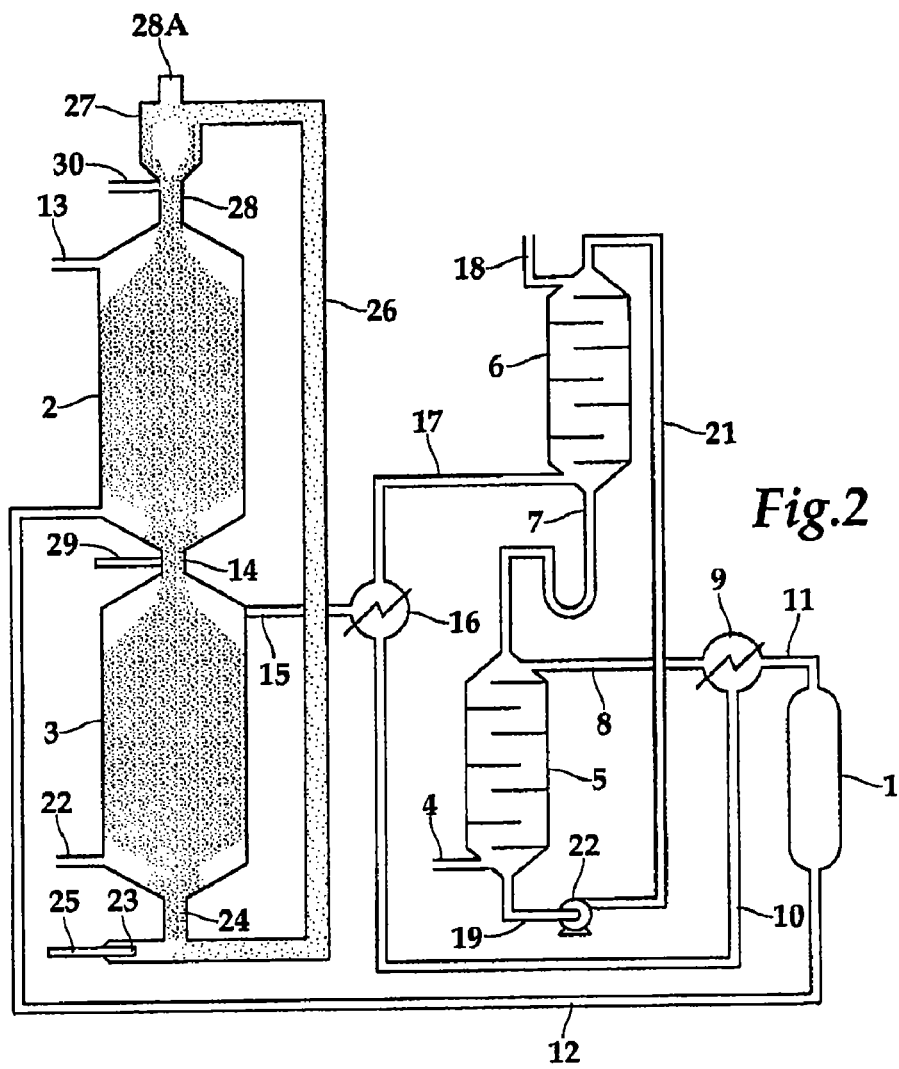
FIG. 2 is a schematic diagram of an alternative embodiment of the inventive process.

If the encapsulated pellets are made spherical and prove strong enough they can be moved around in a system as shown in FIG. 2.

Referring to FIG. 2, methane is fed through line 4 to striper 5, striping halide from halide solution coming down from striper 6 through line 7. Methane with halide vapor from striper is led to saturation vessel 9 through line 8 where the balance of the required halide is added through line 10. The resulting mixture of methane and halide is fed through line 11 to reactor 1 where methyl halide and through line 8 where the balance of the required halide is added through line 10. The resulting mixture of methane and halide is fed through line 11 to reactor 1 where methyl halide and hydro-halide acid are produced. The methyl halide and hydro-halide acid are led through line 12 from reactor 1 to bottom of reactor 2 where they meet in countercurrent the magnesium base reacting to form a product gas containing methanol, di-methyl ether and ethylene which are exhausted from reactor 2 through line 13. Metal halide formed in reactor 2 is led by gravity to lower reactor 3 through line 14 where it meets a counter flow of oxygen or air forming halide which together with excess oxygen or air are led through line 15 to cooler 16 where the halide condensed is led through line 10 to saturation vessel 9.

Line 17 leads excess oxygen or air to striper 6 where it meets a countercurrent flow of solvent which strips halide from gasses which leaves striper 6 through line 18 to exhaust to the atmosphere. Solvent loaded with halide flows downwardly through line 7 to striper 5. Spent solvent is led through line 19 to pump 20 which pumps solvent to striper 6 through line 21. Oxygen or air is fed into reactor 3 through line 22. Magnesium base produced in reactor 3 is led to ejector 23 through line 24 which is fed with air through line 25 and conveys the magnesium base through line 26 to cyclone 27 which empties the basic magnesium through line 28 to reactor 2 and exhausts air to the atmosphere through line 28. Steam through line 29 into line 14 prevents gasses from reactor 2 to pass into reactor 3. Steam through line 30 prevents gasses from cyclone 27 to pass into reactor 2.

EXAMPLE 1

Highly porous encapsulated magnesium oxide catalyst of one embodiment of the invention can be made as follows 50 parts by weight of fine powder magnesium stearate $Mg(C_{18}H_{35}O_2)_2$ are well mixed with 50 parts by weight of fine powder bentonite and enough water added to form a doughy mixture which is then kneaded until smooth. The mixture is then pelletized and air dried at typical room temperatures. Once dried the pellets are calcined at to a minimum temperature of 600 degrees C. to form highly porous magnesium oxide, encapsulated in a ceramic clay matrix.

Highly porous encapsulated magnesium oxide can be made as follows 50 parts by weight of fine powder magnesium citrate, $Mg(C_6H_5O_7)_2$—$14H_2O$, are well mixed with 50 parts by weight of fine powder kaolin, 1 part by weight of ground X-type zeolite in the acid form and 50 parts by weight of water added to form a dough which is then kneaded till smooth and then pelletized and dried. Once dried the pellets are calcined to at least about 600° C. to form the magnesium oxide encapsulated in a matrix of hard clay or porcelain. The proportions of magnesium citrate to clay can vary. The higher the proportion of clay, the harder the pellet but the lower the capacity for halide or alcohol production, and thus, for alkene production. The pellets can be made spherical or in any other shape, by hand or machine, known in the art. Other types of clays and inorganic porous agglutinates, as are known in the art, may be used as the encapsulating material in embodiments of the invention.

We claim:
1. A process to produce one or more compounds comprising:
halogenating one or more alkanes with one or more halogens to form one or more alkane halides and one or more hydrogen halide acids; and
reacting the alkane halides and hydrogen halide acid with one or more encapsulated metal oxide catalysts to form one or more compounds selected from the group of alkyl alcohols, ethers and alkenes and one or more metal halide;
wherein the one or more encapsulated metal oxide catalysts comprises a pelletized and calcined mixture of clay and an organic metal salt and further wherein the one or more alkanes are selected from methane, ethane, propane and butane.
2. The process of claim 1 wherein the one or more alkanes is methane.

3. The process of claim 1 wherein the one or more halogens are selected from chlorine, bromine, and fluorine.

4. The process of claim 3 wherein the one or more halogens is chlorine

5. The process of claim 3 wherein the one or more halogens is bromine.

6. The process of claim 1 wherein the one or more alkane halides is methylchloride, methylbromide, or a mixture thereof.

7. The process of claim 6 wherein the one or more alkane halides is methylchloride.

8. The process of claim 6 wherein the one or more alkane halides is methylbromide.

9. The process of claim 1 wherein the one or more compounds selected from the group of alkyl alcohols, ethers and alkenes are selected from the group of ethylene, propylene, 1-butylene, 2-butylene, and combinations thereof.

10. The process of claim 1 wherein the one or more compounds selected from the group of alkyl alcohols, ethers and alkenes is dimethylether.

11. The process of claim 1 wherein the one or more compounds selected from the group of alkyl alcohols, ethers and alkenes is methanol.

* * * * *

UNITED STATES PATENT AND TRADEMARK OFFICE
CERTIFICATE OF CORRECTION

Page 1 of 1

PATENT NO. : 7,968,755 B2
APPLICATION NO. : 12/874185
DATED : June 28, 2011
INVENTOR(S) : Jorge Miller and Luisa Kling Miller It is certified that error appears in the above-identified patent and that said Letters Patent is hereby corrected as shown below:

Column 5, Lines 12 and 20, replace the word "trough" with --through--.

Column 5, Lines 13, 51 and 53-54, replace the word "striper" with --stripper--.

Column 6, Lines 4, 6, 8, and 9, replace the word "striper" with --stripper--.

Column 5, Line 52, replace the word "striping" with --stripping--.

Column 7, Line 4, Claim 4, add a --.-- following the word chlorine.

Signed and Sealed this
Eighteenth Day of October, 2011

David J. Kappos
*Director of the United States Patent and Trademark Office*